(12) United States Patent
Brown

(10) Patent No.: US 6,275,340 B1
(45) Date of Patent: Aug. 14, 2001

(54) ANESTHETIC ALLEVIATION BY SENSORY STIMULATION

(76) Inventor: Rayford K. Brown, 4004 Cloudcrest Dr., Plano, TX (US) 75074

(*) Notice: Subject to any disclaimer, the term of this patent is extended or adjusted under 35 U.S.C. 154(b) by 0 days.

(21) Appl. No.: 09/488,959

(22) Filed: Jan. 21, 2000

(51) Int. Cl.⁷ .............................. G02B 27/14; G02B 3/00; G02F 1/133
(52) U.S. Cl. ................... 359/630; 359/631; 359/632; 359/642; 349/11
(58) Field of Search .................. 359/630, 631, 359/632, 642, 649; 349/1, 11, 58

(56) References Cited

U.S. PATENT DOCUMENTS

| | | | |
|---|---|---|---|
| 4,093,347 | 6/1978 | La Russa | 350/174 |
| 4,282,864 * | 8/1981 | Pizer | 600/26 |
| 4,475,035 | 10/1984 | Eaton et al. | 250/236 |
| 4,936,657 | 6/1990 | Tejima et al. | 350/331 R |
| 5,005,930 | 4/1991 | Morin | 350/333 |
| 5,278,532 | 1/1994 | Hegg et al. | 345/7 |
| 5,302,985 | 4/1994 | Kennedy et al. | 353/122 |
| 5,311,220 | 5/1994 | Eichenlaub | 348/55 |
| 5,333,072 | 7/1994 | Willett | 359/41 |
| 5,412,419 | 5/1995 | Ziarati | 348/61 |
| 5,416,541 | 5/1995 | Fog | 353/119 |
| 5,500,747 | 3/1996 | Tanide et al. | 359/40 |
| 5,517,278 | 5/1996 | Takahara et al. | 354/471 |
| 5,538,579 | 7/1996 | Miyatake et al. | 359/634 |
| 5,639,152 | 6/1997 | Nelson | 353/119 |
| 5,642,927 | 7/1997 | Booth et al. | 353/119 |
| 5,706,070 | 1/1998 | Reich et al. | 351/201 |
| 5,709,677 | 1/1998 | Slatkine | 616/17 |
| 5,782,547 | 7/1998 | Machtig et al. | 353/28 |

FOREIGN PATENT DOCUMENTS

| | | |
|---|---|---|
| 3923140 | 11/1990 | (DE) . |
| 19538272 | 2/1997 | (DE) . |
| WO 98 10584 | 12/1998 | (WO) . |

* cited by examiner

Primary Examiner—Ricky Mack
Assistant Examiner—Michael A. Lucas
(74) Attorney, Agent, or Firm—Christopher J. Whewell

(57) ABSTRACT

A device according to the invention is useful for providing viewable images and sounds to persons undergoing medical treatments, including radiotherapy, cosmetic, and other surgeries. According to the invention, there is provided an image source means, a Fresnel lens and an enclosure which is adapted to contain the image source means and Fresnel lens, and which also includes a means for attaching the enclosure to existing equipment associated with a medical procedure, wherein the existing equipment includes a flat surface portion upon which the patient is intended to lay in either a supine or prone position. A device according to the invention is especially useful in rendering children immobile during radiotherapy without the need for administration of anesthetics which are otherwise necessary to keep the child from shifting position while the therapy is administered. Elimination of anesthesia according to the invention improves the quality of life for the patient and his/her family, and imposes no burden on vital organs such as the liver, which is otherwise attendant to the administration of anesthetics.

32 Claims, 7 Drawing Sheets

ANESTHETIC ALLEVIATION BY SENSORY STIMULATION

This invention relates to a device and method for reducing and in many cases eliminating the need for anesthesia in medical procedures. More particularly, it relates to a device which provides visual images and sound impulses to patients receiving radiotherapy or other therapies, while the patient is resting in either a prone or supine position. A device according to the invention is adapted to be retrofitted for use with existing hospital equipment.

BACKGROUND

A large number of diseases which plague the human organism are known to persons in the health care and related fields. Within the large number of known diseases are several sub-classes into which the various ailments may be categorized, including cardiovascular, renal, pulmonary, dermal, cerebral, lymphatic, hepatic, carcinomic, etc. The several specific diseases within these classes and others are in general treatable by techniques specific to the particular disease in consideration; however, a common thread in the field of the treatment of diseases is that some form of anesthesia is typically employed by physicians when operating on patients, in order to make the procedure feasible, for most human patients are unable to bear the physical pain and/or emotional distress associated with operational procedures employed, and in the absence of anesthesia would tend to move themselves about, thus making surgeries and other operational procedures impossible for all practical purposes.

The field of anesthesiology, in a broad sense, is one which dates back perhaps to ancient times, when a chemical substance was given to a first person to enable a second person to carry out physical actions on the first person that the first person would not normally permit, owing to instinctive reactions, with the use of alcohol probably being the first anesthetic. Since the advent of modern chemistry in the latter portion of the eighteenth century with the discovery of nitrous oxide by Priestly, and subsequently its effects on humans by Sir H. Davy, a large number of substances either natural, synthetic, or semi-synthetic, that are possessive of anesthetic properties have been identified and utilized as general and/or local anesthetics, including, without limitation, various alkaloidal substances including ecgonine derivatives, morphine derivatives, ethers, alkyl halides, halogenated ethers, derivatives of barbituric acid and thiobarbituric acid, nitrous oxide, steroidal derivatives, procaine, etc.

To be effective as an anesthetic, a chemical substance must be capable of causing the person to whom administered to exist in a state of consciousness where physical actions such as lacerations no longer cause a pain response which would otherwise manifest in instinctive bodily movements away from the source of the pain. The anesthetic must also be statistically safe to use on human subjects so that the anesthetic substance does not cause complications or lead to abnormal vital signs or even death of the patient. Ideally, anesthetics would be short-acting on a relative time scale, being effective only for the duration of the surgery or other medical procedure, and would have no after effects on the consciousness of the person subject to medical treatment.

In actual practice, the various identified anesthetics possess some degree of undesirability with respect to one or more physical properties and actions, and the most suited anesthetic for a given medical procedure is one which has the most desirable overall characteristics. Still, there are essentially no anesthetics which are completely devoid of the requirement for pretreatment conditioning and after effects on the mental and/or physical state of the patient. In cases where frequently repeated medical procedures are required, in particular radiotherapies for carcinomas, a patient receiving chemical anesthetics spends a great deal of time preparing for the anesthesia and experiencing the after-effects of the anesthesia administered. In many cases, this translates to the loved ones and family of the affected person being unable to carry out normal relations with that person during the time which they are experiencing the after effects of the anesthesia, or extended time periods of fasting required prior to treatment and contending with disrupted sleep patterns caused by repeated daylight anesthesia treatments. In cases where the persons being treated are suffering from a disease which has a high statistical death rate within a short time period, such as a year or even a few months, the loss of normal interaction with the affected person becomes a hindrance to the quality of life and mental well-being of all persons involved. Therefore, it is desirable to provide for the complete elimination of the use of anesthetics when possible to enhance the overall quality of life for persons suffering from ailments which require frequent, repeated therapy normally accompanied by anesthesia. This is especially true in the case of younger persons whose mental faculties are in a stage of development which may be more negatively affected by the repeated use of anesthetics over a time period of 6 months to a year.

Finally, it is well known that the liver is an indispensable organ within the human body whose function includes removal of various impurities from the blood stream by at least three known mechanisms. The liver includes special cells known as Kupffer cells that are responsible for engulfing and digesting dead cells, cancer cells, yeasts, viruses, bacteria, parasites, artificial chemicals (including anesthetics and their metabolites), incompletely digested or denatured proteins and other dangerous foreign particles. If the Kupffer cells are worked too hard, such as by the repeated administration of anesthetics, then the Kupffer cells are likely to become less available to cleanse the system of the other normally-encountered biological and chemical species which must be removed to maintain "normal" health, and the subject individual may begin to show symptoms traditionally associated with hepatic dysfunction, which symptoms are varied but include: excessive body mass, abdominal bloating, poor digestion, frequent fatigue, headaches, unpleasant moods, bad breath and coated tongue, irritable bowel syndrome, sluggish metabolism, an overburdened immune system, high cholesterol, gall bladder disease, a fatty liver, allergies, high blood pressure, excessive body heat, sugar cravings, and the inability to lose weight. Therefore it is desirable for all persons whenever possible to minimize the exposure of the liver to chemical substances foreign to the body. This is especially true for persons undergoing repeated therapies such as radio therapy which is known to generate a myriad of biological species, free radicals, and other chemical species known to burden the liver.

It is therefore an object of this invention to provide a means by which persons who suffer from ailments which require repeated therapy regiments (including radio therapy) and attendant anesthesia can undergo treatments without the need for administration of anesthetics prior to the procedure.

It is also an object of the invention to provide a means by which persons who suffer from ailments which require repeated therapy regiments and attendant anesthesia can undergo treatments without the need for administration of anesthetics prior to the procedure, wherein the means is retrofittable to existing equipment commonly found in hospitals and treatment facilities.

It is a further object of the invention to increase the overall health level of a person subject to repeated procedures normally requiring anesthesia by elimination of the need for such chemical anesthetics, which lessens the load on the liver in order to render it more efficient at fighting the underlying cause of the ailment, in addition to carrying out its normal functions.

Through use of a device and means according to this invention, the foregoing objects may be accomplished, providing a higher quality of life for persons undergoing procedures requiring anesthesia on a regular basis.

SUMMARY OF THE INVENTION

The present invention provides a device useful during administration of radiotherapy, surgeries, and other medical procedures on patients. In one preferred form the invention comprises an enclosure portion that has a floor portion, two side wall portions, a first end wall portion and a second end wall portion. There is an image source means located within the enclosure portion, in which the image source means has a flat surface on which images are displayed. A device according to the invention also includes an essentially planar Fresnel lens disposed in a parallel configuration with respect to the flat surface of the image source means. The whole enclosure includes a means for its being attached to existing equipment associated with a medical procedure, in which the existing equipment includes a flat surface portion. Through use of the invention, a patient resting upon the flat surface portion of the existing equipment may view video images displayed by said image source means and hear sounds provided by speakers when the enclosure includes these. Optionally, the speakers may be externally located, or may consist in an earphone set.

DETAILED DESCRIPTION

Figure 1A:
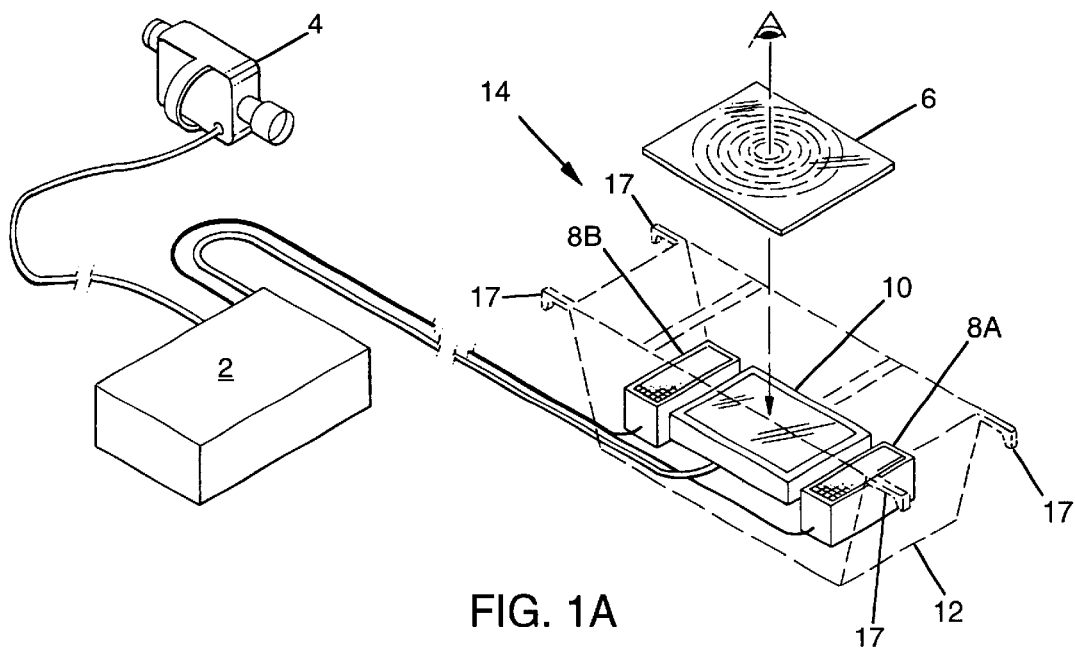
FIG. 1A is a schematic drawing showing a direct viewing device according to the invention.

Referring to the drawings and initially to FIG. 1A there is shown a direct viewing device 14 according to the invention. Here is shown a source of video images and/or sound impulses 2, which may be any source of video images known to those skilled in the art, including, without limitation, a video cassette recorder ("VCR"), DVD player, cable TV, random access digital hard disk recorder/playback system, etc., and which may be adapted to receive images or sound impulses from external sources, such as a video camera 4 or other image transducing device. The direct viewing device 14 comprises an enclosure portion 12, which is adapted to be disposed about existing hardwares associated with radiotherapy currently present in treatment facilities and hospitals. The enclosure portion is, in one embodiment of the invention, shaped in general like a box in rectangular-solid form, including a bottom portion, two side wall portions, and two end wall portions. In yet another preferred form of the invention, the enclosure portion comprises one or more trapezoidally-shaped side wall portions.

The invention includes a means for attaching the enclosure or the device as a whole 14 to existing equipment used in radiotherapy, which may comprise four projecting portions, that are hooks 17 in one embodiment, disposed at the upper corner portions of the enclosure, wherein the hook portions are adapted to cooperate with rails that are commonly employed as an integral part of support structures associated with medical procedures. In an alternate form of the invention, the hook portions are replaced by four prongs which are flat on their bottoms. In yet another alternate form of the invention, the means for attaching the enclosure means to the existing equipment in the treatment facility comprises conventional fasteners, which may be any fastening means known to those skilled in the art including, without limitation, screws, nuts and bolts, serrated straps, straps, hook and loop type fasteners, welds, snaps, braces, brackets or the like.

It shall be appreciated by one of ordinary skill in this art after reading this specification and the claims appended hereto that the invention embraces the use of an enclosure means of any geometric shape, provided that it contains a volume in which the display means, Fresnel lens, and optionally a reflective surface is substantially contained, including hemispherically-shaped enclosures. Therefore, for purposes of this specification and the appended claims the word "enclosure" is any means that is capable of enclosing the aforesaid elements, regardless of its geometric configuration, provided that its configuration does not in any way interfere with, absorb, or scatter a beam of radiation that is to be applied to the patient. Preferably, the materials of construction of the enclosure according to the invention are selected to be translucent to the radiation employed in the medical procedure used. Alternatively, one practicing the invention may use materials which block radiation, provided that voids are designed into the device's structure to permit the unimpeded passage of radiation to selected areas.

The enclosure includes a hollow portion in its interior into which hollow portion is housed the necessary elements for making the device as a whole operational. These elements include an image source means 10 upon which images conveyed to the screen are displayed for viewing by a patient. The image source means 10 may be any means known in the art upon which images may be displayed, without limitation, cathode ray tubes (CRT's), flat surfaces upon which projections are made (i.e., movie screens), flat panel screens which utilize various technologies known in the art, liquid crystal displays, etc. The image source means 10 is a liquid crystal display in a preferred form of the invention. Therefore, for purposes of this specification and the appended claims, the words "image source means" embraces all such means known in the art upon which visual images may be generated or displayed. An image source means includes a display surface, which, on a cathode ray tube, is the surface of the screen where the phosphor is disposed. Typically, the display surface is essentially flat, such as in the case of flat-panel displays and many television sets. However, often the surface on which cathode ray tubes display images are slightly convex. This invention embraces the use of image source means having both flat and curved display surfaces. It is generally preferable that this results in the Fresnel lens being disposed in a substantially perpendicular configuration with respect to a normal line that projects outward from about the middle of the display surface, which means that the surface of the Fresnel lens is preferably disposed perpendicular to the direction at which the images are projected from the image source means. The enclosure may be mounted such that the distance between the patient's eyes and the enclosure means is less than 1 meter.

Also disposed within an enclosure in another form of the invention is at least one, and preferably a plurality, of speaker means 8 for providing sound impulses, which may be any signal in the audible range of the human ear, between about 20 and 20,000 cycles per second (cps). Various speakers are known in the art which are capable of transducing sound impulses communicated to the speaker as electrical signals, into sound energy. In their simplest form speakers comprise a coil of wire in mechanical contact with a conical vibratable medium (which is often paper or metal), and wherein the coil is disposed about a permanent or other magnet such that the cone is caused to move in response to the varying amplitude of the electrical impulses supplied to the coil. The present use of the term "speaker means" is intended to embrace all speaker means known to those skilled in the art.

A Fresnel lens 6 is also an element of an assembly according to the invention. The Fresnel lens element is well known in the art of lenses, and in the instant case is preferably disposed between the viewing screen and the eye of the patient viewing the images on the screen. The Fresnel lens serves to shorten the optical path. In the instant invention, the Fresnel lens enlarges the images to the point that the patient's entire field of view is embraced by the images displayed on the screen. The Fresnel lens therefore increases the efficiency of the transmittal of the images displayed on the screen to the patient viewing the images.

Figure 1B:
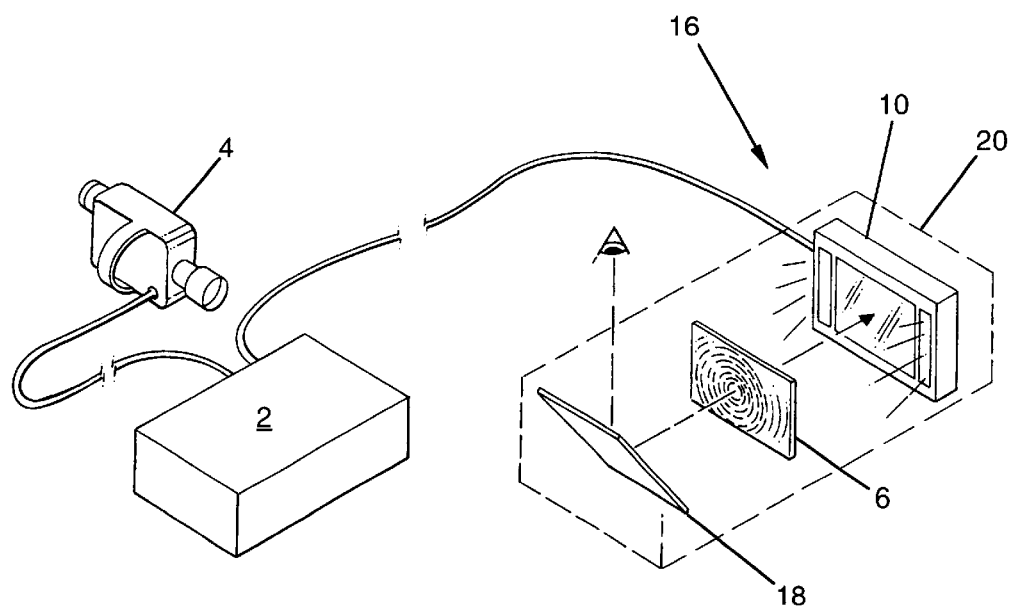
FIG. 1B is a schematic drawing showing a reflective viewing device according to the invention.

In FIG. 1B is shown an indirect viewing device 16 according to the invention. An indirect viewing device according to the invention comprises an enclosure portion that is essentially a rectangular solid in its geometry, and having a hollow interior portion into which the various necessary cooperating elements, including an image source means 10 and Fresnel lens 6, are housed. The indirect viewing device is termed "indirect" because the images displayed on the image source 10 are re-directed by means of a reflective surface 18 (which is preferably a mirror) prior to their receipt by the eye of the viewing patient. The Fresnel lens portion 6 may be disposed between the reflective surface 18 and the image source means 10, or, in an alternative form of the invention, the reflective surface 18 may be disposed between the image source means 10 and the Fresnel lens 6, with the former arrangement being most preferred when an enclosure 20 containing these elements in cooperative connection is employed for a patient resting in a supine position. An indirect viewing device according to the invention as pictorially displayed in FIG. 1B also includes a source of video images and/or sound impulses 2, and may further include a video camera or other source. Although not pictured in FIG. 1B, the enclosure portion 20 may also contain one or more speaker means when desired. In various alternate forms of the invention, one or more speaker means may be located in any desired position within the room in which a procedure is carried out according to the invention, provided that the patient is able to hear the sounds emitted from the speaker means, for example, one or more speaker means may be affixed to the frame of the surface upon which the patient rests during the procedure.

Figure 2A:
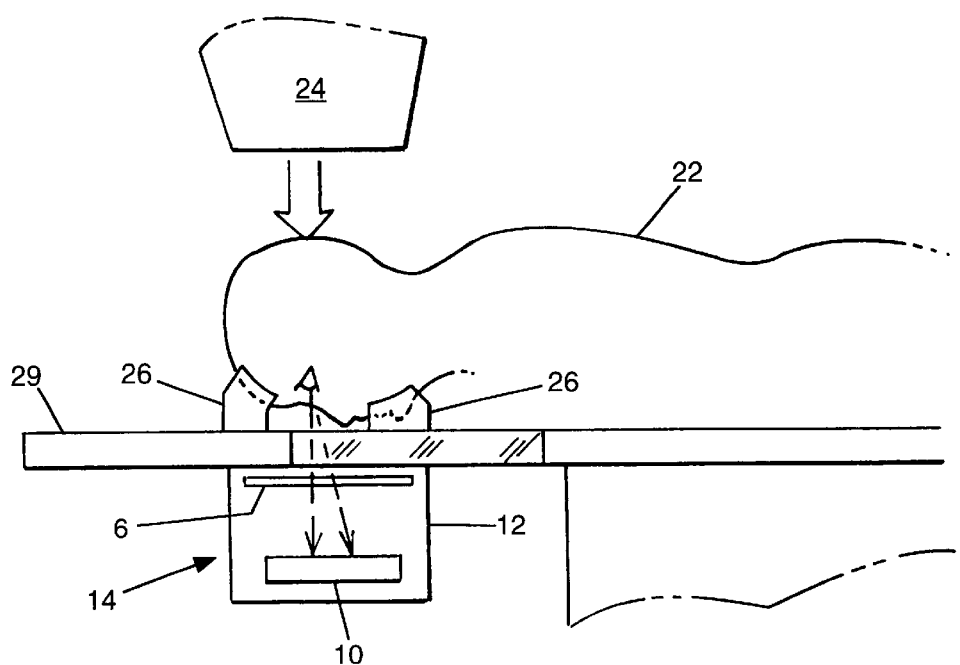
FIG. 2A is a side view of a patient in the prone position viewing images displayed on a direct viewing device according to the invention.

In FIG. 2A a patient receiving radiotherapy is shown in a prone position, disposed about a flat surface portion 29. A device according to the invention is designed to be retrofittable to existing equipment in treatment centers. One common piece of such existing equipment comprises a table portion such as that depicted in FIGS. 2A and 2B, which is manufactured by the Oncology Systems Division of Varian Medical Systems, Inc. of Palo Alto, Calif. Referred to as a "couch" by those in the industry, one especially preferred table means for use in conjunction with a device according to the invention is that sold by Varian under the common or trade name of "Extended Travel Range Couch". However, by the versatility and wide possible selection of the means for attaching a device as a whole according to the invention (such as 17) to existing equipment used in radiotherapy, a device according to this invention is readily adaptable to be utilized with any existing piece of equipment useful in various medical procedures. This is especially true when a support frame is utilized in conjunction with a device according to the invention, as will be described in more detail elsewhere herein for cases where a patient is resting in a supine position. The number of surgical procedures and other medical treatments which are carried out while the patient is in a supine position is large. When a support frame is provided it enables mounting of a viewer above the patient so they may view images while medical actions are carried out.

FIG. 2A depicts the patient 22 in a prone position resting atop a flat surface portion 29, wherein the flat surface has a hole disposed through it that enables the patient to view images provided on a direct viewer located immediately beneath the flat surface of the flat surface portion 29. This configuration is especially preferred when the patient is receiving radiotherapy on a couch 29 that has space in its interior for the direct viewer.

The mechanism by which a device according to the invention works is not certain; however the device has been used in the radiotherapy of children who are afflicted with cerebral and/or spinal carcinoma, conditions which traditionally have required administration of anesthesia prior to the procedure to ensure the patients do not move about excessively during the treatment and cause the treatment to be administered to sites on the patient that are overlapping which can result in radiation overdoses. It is believed that merely being in the environment of a treatment facility and knowing that one is about to undergo therapy raises the anxiety level in a person to the point that his/her mind is concentrating on the facilities' equipment, and the fear of the unknown becomes a factor in the patient's mental state. The captivating effect of moving images and sounds associated therewith is well-known by most persons having offspring who watch television shows. It is believed that when a person's attention is directed to a television set, his/her perception of other sensory stimuli is lessened in proportion to his/her interest level in the images and sounds provided by the television. The present invention provides a means for providing images which captivate the mental faculty of a patient viewing the images to the point that other external sensory stimuli do not impact the mental state of the patient viewing the images.

In the case of small children, this task is readily accomplished by providing images of a favorite cartoon while the radiotherapy is administered, although other images such as home movies, views and sounds of nature with music or "white noise", etc. may be used with equal effect. In the case of small children with a natural tendency to move about, the use of a device according to the invention has been found repeatedly, through actual clinical use of devices according to this invention, to be especially useful for captivating their attention sufficiently to render the administration of anesthetics normally used to immobilize the child to be no longer necessary. Therefore, the quality of life for the child and immediate family is enhanced (especially in cases of frequent, repeated therapy), since the patient requires no special preparation and is not in a drowsy state following the treatment as is otherwise the case.

Figure 2B:
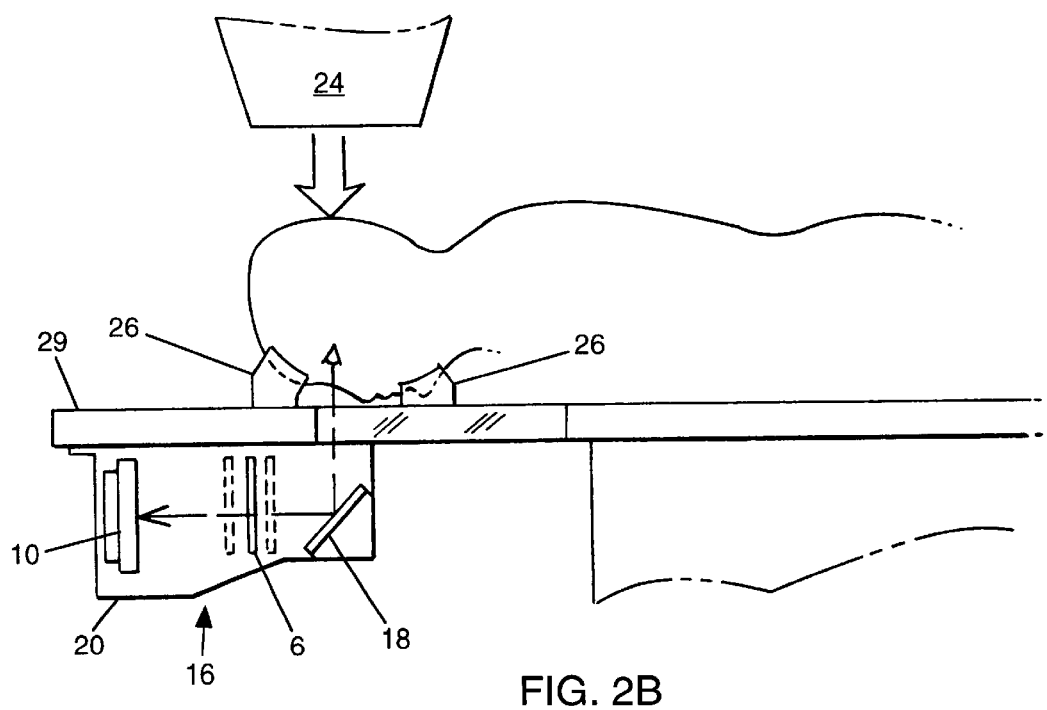
FIG. 2B is a side view of a patient in the prone position viewing images displayed on a reflective viewing device according to the invention.

FIG. 2B depicts a device according to the invention as being used in a similar mode of radiotherapy as was shown in FIG. 2A, with the exception being that an indirect viewing device is utilized instead of the direct viewer. This partially shows the versatility of an indirect viewer according to the invention, for the same indirect viewer of FIG. 2B may also be used with a support frame for a patient resting in a supine position, as will be shown in greater detail further on.

Figure 3:
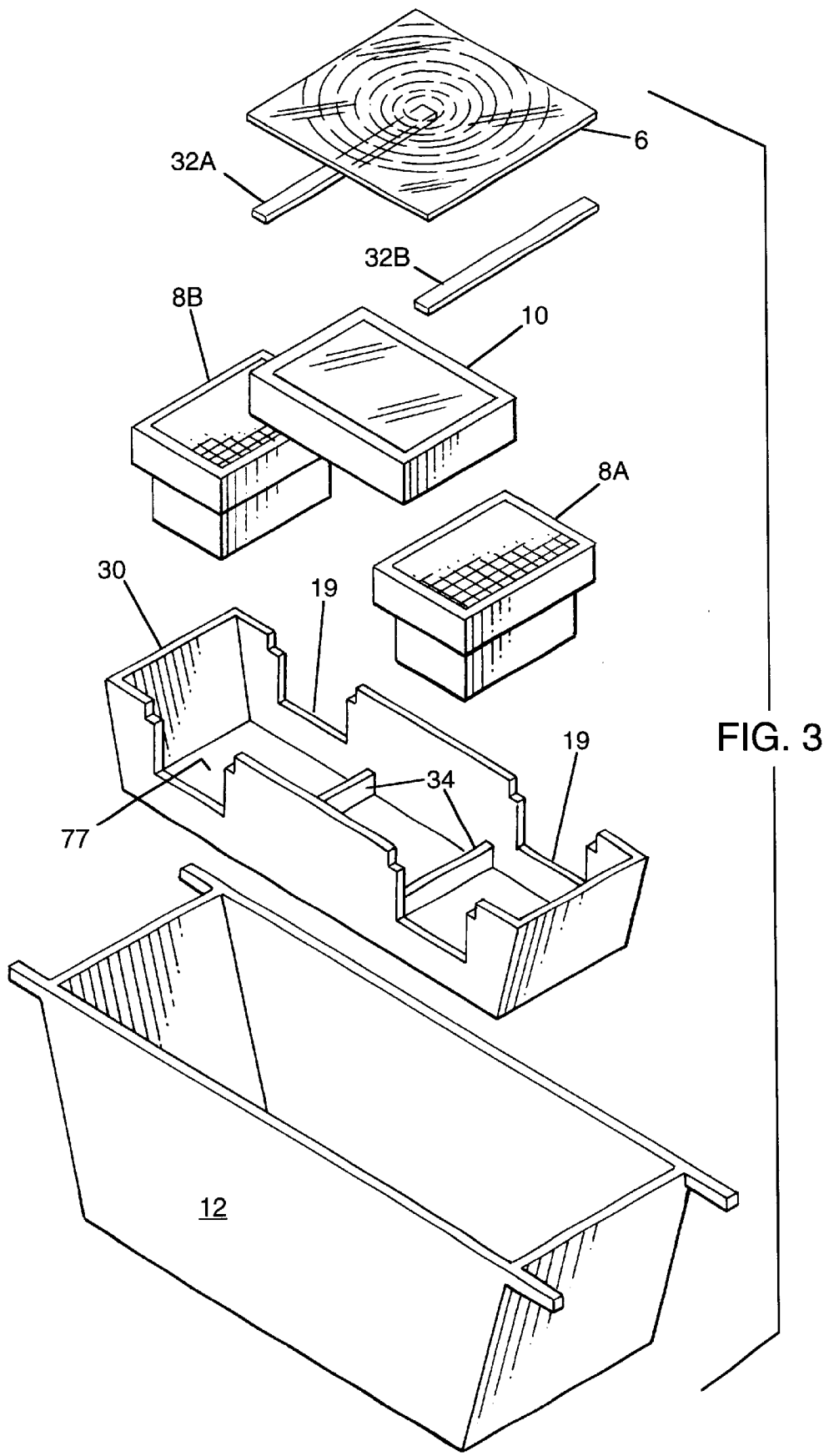
FIG. 3 is a perspective exploded view showing the various components of a direct viewing device according to a preferred form of the invention.

FIG. 3 shows the respective components of a direct viewer according to the invention, including the enclosure portion 12, speaker means 8A and 8B, image source means 10. Fresnel lens 6, supports 32A and 32B, supports 34 which also function to define a location between which the screen means is to be disposed, and a framework insert 30 that is adapted to receive the various aforesaid components and maintain them in rigid position within the enclosure. The framework insert includes a floor portion 77. The insert portion has slots 19 carved into the first and second wall portions of the framework insert portion 30 in order to receive the speaker means. Although depicted in FIG. 3 as cut-outs adapted to receive speaker means having the geometries shown for the speaker means, other shapes of the cut out portions are within the scope of the invention and readily apparent to one of ordinary skill after reading this specification and claims, to the extent that the cut out portions match the contours of the speaker means that is to be held in rigid position. The support portions 32A and 32B provide for secure support of the Fresnel lens. In one form of the invention, these spacer portions are shaped like an "L" on one side and a "U" on its side on the other. Under such an arrangement, the Fresnel lens may be slipped into the "U" and then dropped on the leg of the "L". Preferably, in this embodiment the lower leg of the "U" is longer to facilitate insertion of the Fresnel lens.

Figure 4:
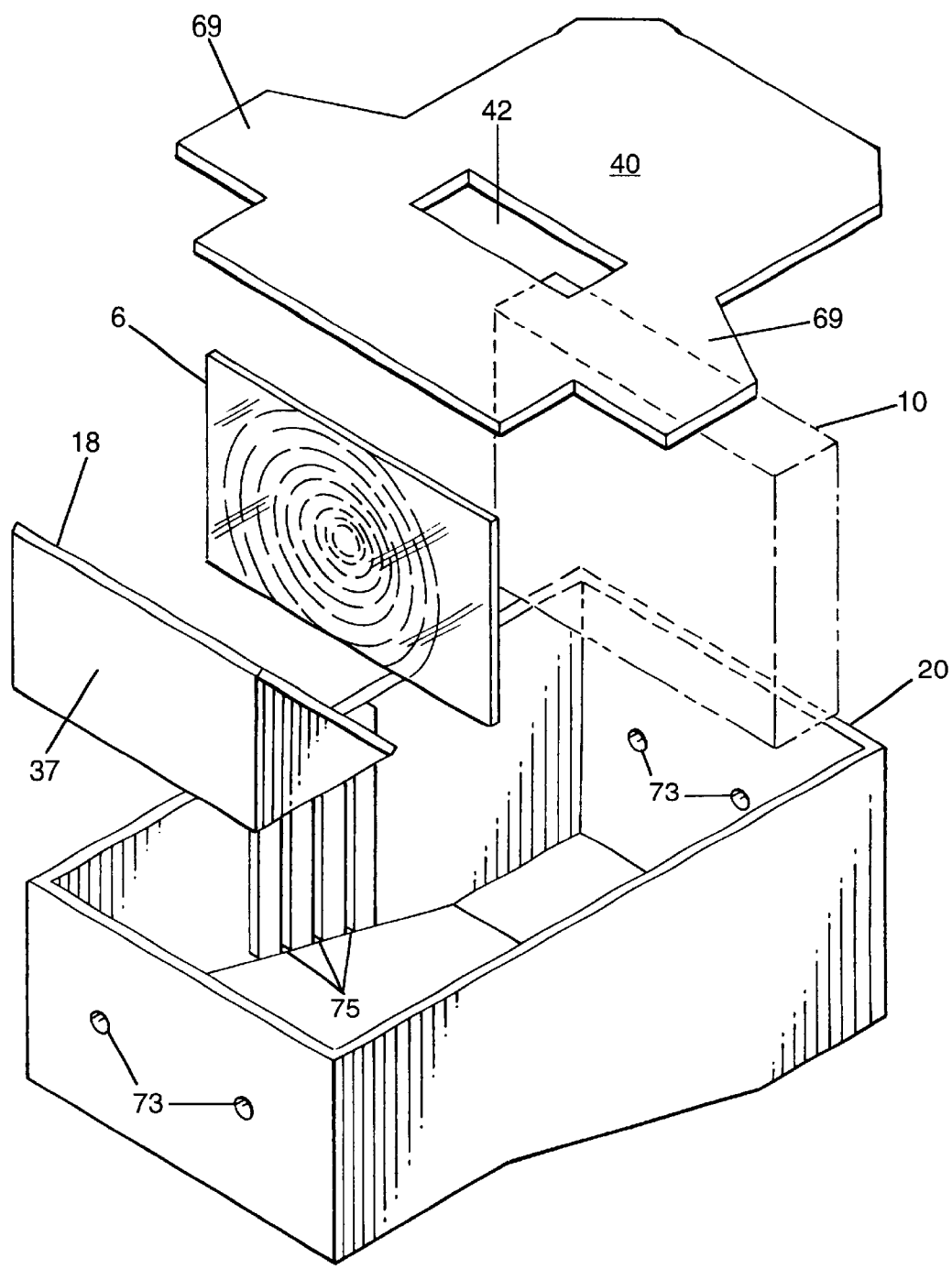
FIG. 4 is a perspective exploded view (prone position) showing the various components of an indirect viewing device according to the invention.

FIG. 4 shows the various components of an indirect viewer according to a preferred form of the invention. The enclosure portion 20 is adapted to receive the necessary elements of the viewing device, and is equipped with holes 73 for convenient attachment to a support frame such as that shown in FIG. 5. Disposed on the inner walls of the enclosure portion are a plurality of slots 75. Identical slots to those 75 shown are provided on the opposite wall portion, so as to render the enclosure adapted to receive the Fresnel lens 6 and maintain it in a rigid position. The location of the Fresnel lens is thus rendered adjustable by virtue of the ability of one to slide the Fresnel lens in and out of any of the various slots, as desired. This provides a means for focusing the images conveyed to the patient and to render the device useful to persons having a wider range of ocular performance capabilities. The slots may be provided by any means known for providing slots, including, without limitation, machining parallel channels into the construction of the wall of the enclosure itself, or as by attachment of say, rectangular blocks of foamcore to the wall portion of the enclosure, in a parallel configuration with a space between them sufficient to accommodate a Fresnel lens inserted therebetween. The main proviso for the mounting of the Fresnel lens within the enclosure is that its surface be essentially parallel to a normal line that projects outwardly from the display surface of the image source means. Means for mounting planar sheets such as Fresnel lenses are well known in the art, and the present invention contemplates the use of all means for mounting a Fresnel lens which are known in the art, including those which use blocks or strips as just mentioned, clips, fasteners, frames, adjustable fixtures, or the like.

Also shown in FIG. 4 is the reflective surface 18, which is preferably attached to an angled locator means 37 for ease in mounting within the enclosure to divert the viewing angle as desired. The locator means may be any ware, fixture, or the like which is capable of maintaining the reflective surface at any angle between 20 degrees and 75 degrees (and including without limitation every integral degree therebetween, inclusive) with respect to the surface of the screen means. Preferably, the locator means is a block of foam-core to which the reflective means is attached by an adhesive known to those in the art. The image source means 10 and Fresnel lens 6 are also shown in their preferred locations with respect to the reflective means. There is also a cover means 40 that is preferably contoured to coincide with the perimeter of the wall portions of the enclosure to shield the various components that are housed within the enclosure from accidental tangling, physical impact, dislocation or other unwanted relocation. In a preferred embodiment, the cover portion also includes an access hole portion 42 through which a technician may gain access to the components housed within the enclosure, for adjustment or maintenance purposes. The patient is able to view images by virtue of the cover portion having a contour that does not completely cover the entire opening of the enclosure defined by its wall portions, particularly that sufficient space necessary for the passage of viewable images which is disposed between the viewing screen (when supine viewing is desired) or the Fresnel lens (when viewing in a prone position) and the patient's eyes. Preferably, the hole portion is a single hole having a rectangular geometry; however, the present invention contemplates the use of multiple holes of various geometries as well, with the criteria for usefulness being that the patient must be able to view the images without undue eye strain. The cover means is also the preferred location of the means for attaching 69 the enclosure to the flat surface portion 29, which in a preferred form of the invention comprise winglike protrusions as a part of the construction of the cover portion. However, the use of any one or a combination of various other means for attaching the enclosure to existing equipment at treatment facilities are within the scope of the invention, including all fastening means known to those skilled in the art including hinges, brackets, braces, nails, rivets, screws, welds, hook and loop fasteners, etc.

Figure 5:
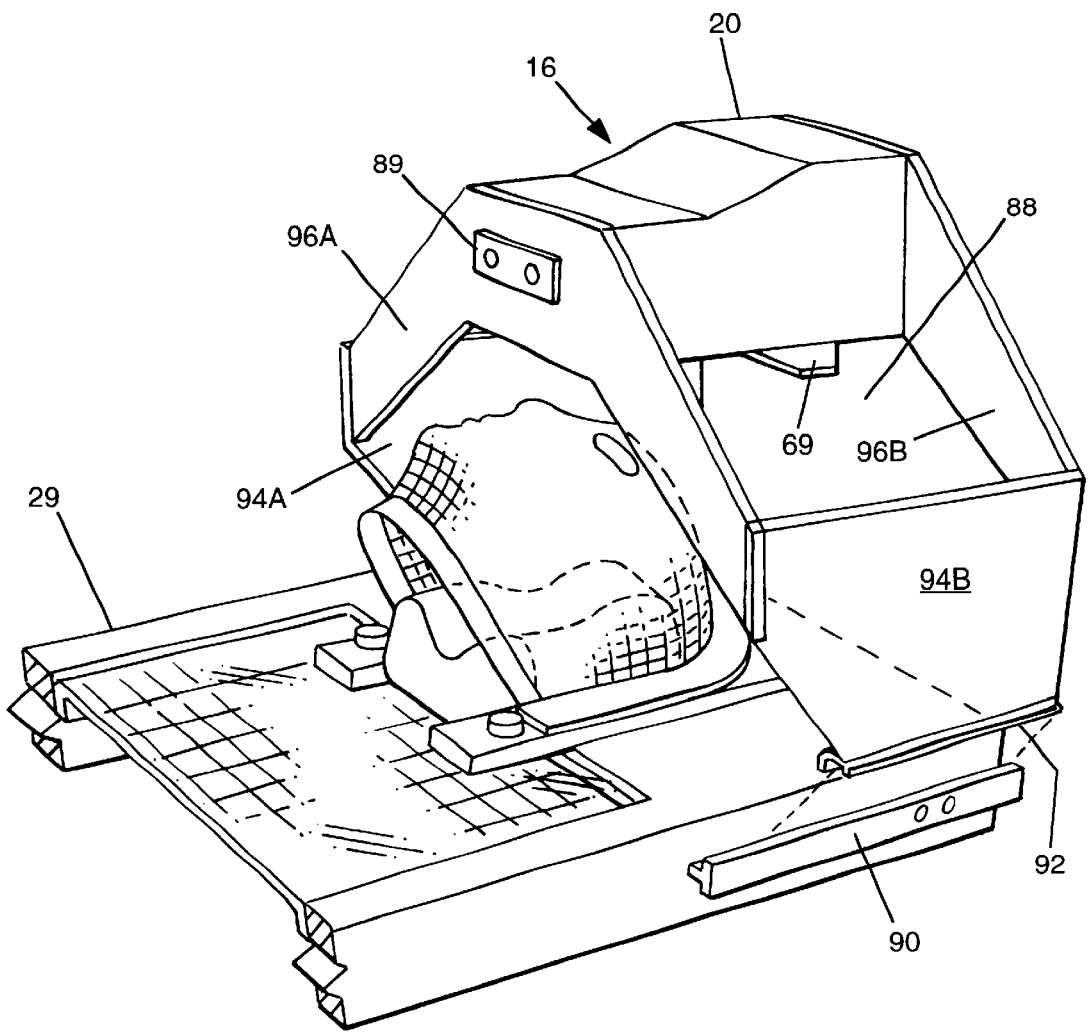
FIG. 5 is a perspective exploded view showing the head immobilizing mask beneath a support frame used in conjunction with a viewing device according to the invention.

FIG. 5 shows an indirect viewer 16 of the invention mounted within a support frame that is resting atop a flat surface portion 29 directly above the position where a patient's head is to be located when the patient is resting in a supine position upon the flat surface portion 29.

Preferably, the support means is configured to receive and be affixed to the enclosure portion 20 using holes in the end portions of the enclosure portion as were discussed previously in FIG. 4, and a cooperative counterpart 89 located on the front portion of the support frame, which may be as simple as a reinforcing plate of Mylar® or a functionally equivalent non-absorbing substance having holes through it which match the distance between the holes 73 on an end wall portion of the enclosure; however, other means for attaching the viewer to a support frame are within the scope of the invention, including hinges, brackets, braces, nails, rivets, screws, welds, hook and loop fasteners, etc. Further, the support frame may be an integral part of the enclosure, as when the support frame as taught herein and the enclosure collectively comprise a unibody assembly which may be produced by, say, injection molding, or any one of a number of means known in the art for combining two structures into one in a single construction.

The support frame preferably consists in a front portion 96A and a rear portion 96B having side wall portions 94A and 94B attached to both, wherein the side wall portions 94A and 94B each include a top edge and a bottom edge. Disposed along the bottom edge of the side wall portions 94A and 94B are means for attaching 92 the support frame to the flat surface portion 29, which are preferably channels that are complementary to a rail portion 90 disposed about the external side of the flat surface portion 29. Such an arrangement provides for rigid support of the support frame while also permitting its easy removal/adjustment, inasmuch as the rail portion 90 transverses the entire length of the table surface. Although the entire construction of the device according to the invention is preferably translucent to the radiation source used (excepting the display means and mirror when a mirror is used), an added feature of the arrangement shown is the inclusion of a void region 88, to which there may be a corresponding second void region symmetrically located with respect to the centerline of the enclosure of the viewing device which is not visible in FIG. 5 owing to the perspective view. It is through these void regions that radiotherapy may be directed for application to the cranial portion of the patient. In the absence of such voids, the structural portions of the support frame would serve to block or scatter any attempted radiotherapy applied when materials of construction that are not translucent to the radiation employed are utilized, which would render any such support frame less effective or ineffective in the regard taught herein. Although disclosed according to a preferred form of the invention, the support frame may be altered to provide any desired location of void regions, with the only proviso being that the support structure of the device is sufficiently rigid to maintain the enclosure in a position which permits viewing of images by the patient without interfering in any way with the applied radiation. As already briefly mentioned, it is most preferable that the entire construction of the device (excepting the display means and the mirror when a mirror is utilized) be of a material which is translucent to the radiation employed. The most preferred material of construction is foam-core, which consists of two polymeric sheets having a layer of foam sandwiched therebetween, as foam-core materials are well known to those skilled in the art. An alternative preferred material of construction is cardboard, however any material of sufficient rigidity for providing a construction according to the invention which is known to those skilled in the art to be translucent to radiation employed in medical procedures is useful as a material of construction for a device according to the invention.

It is common in practice for those skilled in the art to use several laser beams that create vertical and horizontal beam planes that pass through the isocenter of the treatment beam, for pinpoint accuracy in aligning the treatment beam on the region of the patient's body which is to be exposed to the radiation. Often, the patient is tattooed to assist in the alignment process, or a cradle, rigid mask, or other fixture is employed to aid in making certain the radiation source is accurately poised. In this regard, the side wall portions may be fitted with holes, slots or other voids as necessary to permit the laser beams to pass on to the target region unadulterated by obstruction. In an alternate form of the invention, the width dimension of the side wall portions 94A and 94B may be varied as desired, the amount of variance of which is necessary for a given case being well within the level of skill of one of ordinary skill in the art after reading this specification and the claims appended hereto.

Figure 6:
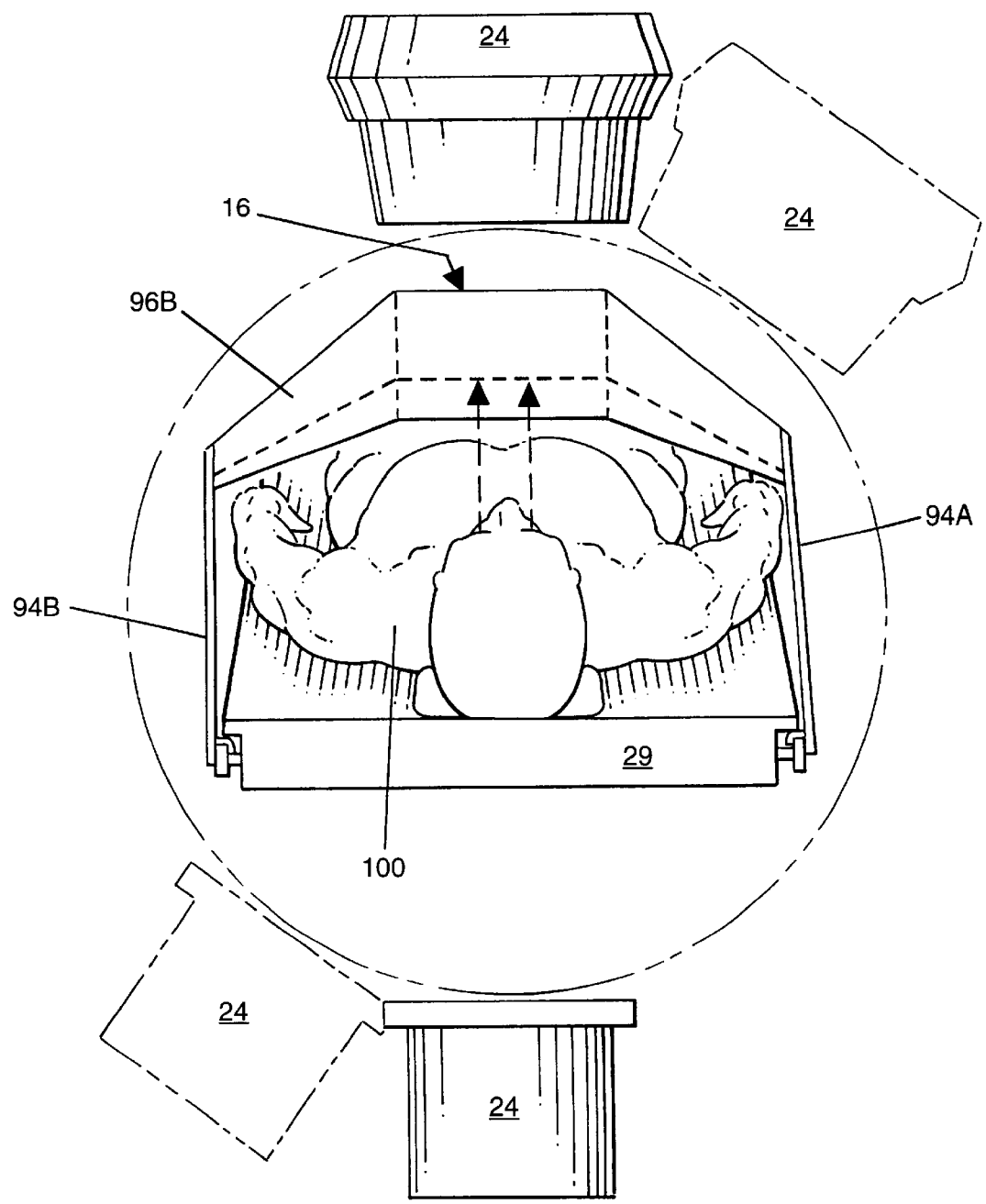
FIG. 6 is an end view showing a device according to the invention about a patient disposed in a supine position.

FIG. 6 shows an end view of a patient 100 resting in a supine position upon the flat surface portion 29 and observing images displayed via a viewer 16 located within a support frame. Here, some of the possible effective locations of a source 24 of the radiotherapy when a device according to the invention is utilized are shown.

Figure 7:
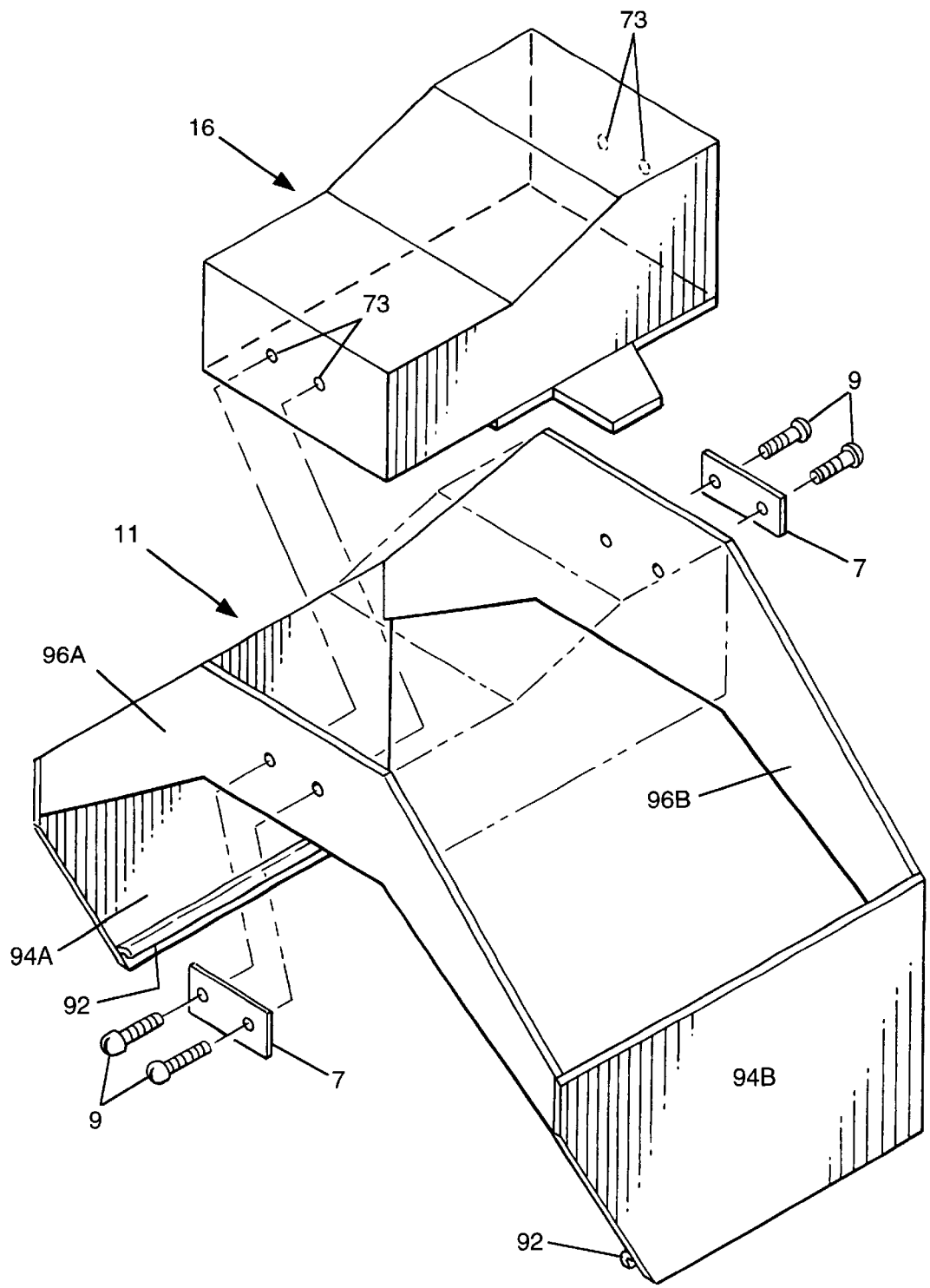
FIG. 7 is a perspective exploded view showing the various components of a support frame and viewing device according to the invention for use by a patient in a supine position.

FIG. 7 shows the preferred means for attachment of a viewer 16 to a support frame 11 according to the invention, which comprises a plurality of fastening means 9, which may be bolts or screws, and a planar piece of reinforcing plate 7 of Mylar® or a functionally equivalent, non-radiation absorbing material, which act through the holes 73 in the end wall portion of the enclosure of the viewing device. The reinforcing plate 7 acts as a torque spreader for load distribution over the foam-core material from which the front portion 96A or the rear portion 96B is fabricated in a preferred form of the invention. In a preferred form of the invention, there are securing plates disposed on the opposite side of the wall portions through which holes 73 are disposed, these securing plates consist of a planar piece of Mylar® in the form of a polygon or circle through which are disposed threaded holes that are spaced and threaded to cooperatively receive the fastening means 9 to securely hold the enclosure within the support.

One design feature of a device according to the invention is the use of particle translucent materials that do not absorb, scatter, or reflect a beam of radiation used. The present invention contemplates the use of holes at desired locations on the device of the invention, for purposes of permitting alignment of the patient in a desired position using a harmless laser beam as a locating means. Placement of holes in the construction of the device is well within the level of skill of one of ordinary skill in the art after reading this specification and the appended claims. Treatment is preferably accomplished through the supports, but not through the mirror, speakers, or display means, and it is often preferable in many of the embodiments of the instant invention in use that the images viewed are not in the path of the beam used for treatment.

Throughout this specification and the claims appended hereto the term "radiotherapy" occurs, and for the purposes of this specification and the appended claims "radiotherapy" means any treatment of the human body brought about through the utilization of electromagnetic energy, including X-rays, gamma-rays, or any other frequency of radiation known in the art as being useful in treating human subjects.

However, while the invention and its use are equally applicable to all forms of radiotherapy, the invention is not limited strictly to use in radiotherapy, but is anticipated as being useful in other surgical and other known procedures for any other ailment, including cosmetic surgery. Thus the present invention can now be readily anticipated as being usefull in a variety of medical procedures, which include any procedure that is not inhibited by the placement of a device according to this invention. Such a "medical procedure" includes radiotherapy without limitation.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A device useful for decreasing the awareness of a patient to his/her surroundings prior to or during administration of a medical procedure which comprises:
   a) an enclosure portion;
   b) an image source means disposed within said enclosure portion, wherein said image source means includes a display surface;
   c) an essentially planar Fresnel lens disposed within the enclosure in a substantially perpendicular configuration with respect to a normal line that projects outward from about the center of said display surface; and
   d) means for attaching said enclosure means to existing equipment associated with a medical procedure so that the images displayed by said image source means is within the view of said patient.

2. A device according to claim 1 wherein the means for attaching includes a support frame that is constructed from a material which is translucent to radiation employed during said medical procedure.

3. A device according to claim 1 wherein said image source means is within 2 meters of the eyes of said patient.

4. A device according to claim 1 wherein said existing equipment includes a flat surface portion adapted to support a patient in a supine or prone position and wherein said means for attaching includes a support frame, so that a patient resting upon the flat surface portion of said existing equipment may view video images displayed by said image source means.

5. A device according to claim 4 wherein the distance between the patient's eyes and the enclosure means is less than 1 meter.

6. A device according to claim 1 wherein the support frame is an integral part of the closure.

7. A device according to claim 1 further comprising a reflective surface disposed within said enclosure portion on the opposite side of said Fresnel lens from said image source means.

8. The device of claim 1 wherein said enclosure portion further comprises a cover portion, wherein said cover portion includes a hole through which images may be viewed.

9. A device according to claim 8 wherein said reflective surface is disposed at an angle with respect to the surface of the Fresnel lens.

10. A device according to claim 9 wherein said angle is between 20 degrees and 75 degrees, including every degree therebetween.

11. A device according to claim 1 wherein said enclosure portion includes a floor portion, two side wall portions, a first end wall portion, and a second end wall portion, wherein each wall portion has one surface facing the interior of said enclosure and one surface facing the exterior of said enclosure.

12. A device according to claim 11 further comprising a cover portion, wherein said cover portion is contoured to completely shroud components contained within the enclosure from physical damage.

13. A device according to claim 12 wherein the means for attaching said enclosure to said existing equipment is attached to said cover portion.

14. A device according to claim 12 wherein the means for attaching said enclosure to existing equipment associated with a medical procedure is an integral part of said cover portion.

15. A device according to claim 12 wherein the inner surfaces of said side wall portions of said enclosure portion include a series of slots adapted to receive said Fresnel lens, to provide adjustability of the location of said Fresnel lens within said enclosure.

16. A device according to claim 12 wherein said support frame includes a front portion and a rear portion, each having end portions, wherein said front portion and said rear portion are connected to one another by two side wall portions, each side wall portion having an upper and a lower edge portion, wherein one of each of the side wall portions is attached to an end portion of each of said front portion and said rear portion.

17. A device according to claim 16 further comprising a portion of said means for attaching the support frame to said existing equipment associated with a medical procedure disposed at said lower edge portion of said side wall portion.

18. A device according to claim 17 wherein a portion of said means for attaching the support frame to said existing equipment associated with a medical procedure is disposed upon said existing equipment.

19. A device according to claim 18 wherein said existing equipment by its design comprises a surface portion upon which a patient may rest in a position selected from the group consisting of: a supine position, a prone position, or a seated position.

20. A device according to claim 16 wherein said enclosure portion is disposed between said front portion and said rear portion of said support frame, and wherein each of said first end wall portion and said second end wall portion of said enclosure are connectively attached to said front portion and said rear portion of said support frame, so as to form a viewing assembly especially adapted for persons in a supine position by virtue of the enclosure being disposed above the cranium of a patient resting on said existing equipment.

21. A device according to claim 20 comprising void regions through which radiotherapy may be applied to the cranium of a patient resting beneath the enclosure, uninhibited by any of the structural features of said support frame.

22. A device according to claim 16 further comprising at least one speaker means disposed within said enclosure.

23. A device according to claim 16 further comprising a source of video images in effective electrical contact with said image source means.

24. A device according to claim 16 wherein said source of video images is selected from the group consisting of cable: TV, VCR, DVD player, cable TV, random access digital hard disk recorder/playback system, video camera, television tuner, and closed circuit television.

25. A device according to claim 1 wherein said Fresnel lens has a cross sectional area that facilitates the line of sight from each eye to view said display surface through the lens.

26. A device according to claim 1 further comprising:

a) a framework insert having a floor portion, wherein said framework insert is adapted to receive said speaker means; and b) at least one speaker means disposed within said insert, wherein said framework is disposed within said enclosure portion such that the floor portion of the framework insert is substantially parallel to said floor portion of said enclosure.

27. A process for enhancing the overall quality of the experience of a medical procedure by a patient which comprises the steps of:

a) providing a device according to claim 1;

b) providing a surface upon which said person is caused to rest;

c) causing images to exist on said image source means, wherein said images are effective to captivate the visual attention of the patient; and d) effecting a medical procedure.

28. A process according to claim 27 further comprising the step of: providing sound impulses to the ears of said person simultaneously with the step of causing images to exist on said image source means.

29. A process according to claim 28 wherein said images are selected from the group consisting of: music videos, cartoons, movies, nature scenes, sports games, sit-coms, news shows, comedy shows, drama, fights, and Shakespearean tragedies.

30. A process according to claim 27 wherein said procedure includes a procedure requiring patient immobility.

31. A process according to claim 27 wherein said procedure includes a procedure selected from the group consisting of: radiotherapy, cosmetic surgery, procedures involving X-Rays, and CT scans.

32. A device useful for decreasing the awareness of a patient to his/her surroundings prior to or during administration of a medical procedure which comprises:

a) an enclosure portion;

b) an image source means disposed within said enclosure portion, wherein said image source means includes a display surface;

c) an essentially planar Fresnel lens disposed within the enclosure in a substantially perpendicular configuration with respect to a normal line that projects outward from about the center of said display surface; and d) means for attaching said enclosure means to existing equipment associated with a medical procedure so that the images displayed by said image source means are within the view of said patient, wherein the means for attaching includes a support frame that includes at least one void through which a target region on the patient's body is accessible for laser alignment of a radiation source used in a medical procedure.

* * * * *